United States Patent [19]

Johnson et al.

[11] Patent Number: 5,019,411
[45] Date of Patent: May 28, 1991

[54] PROCESS FOR BACTERIAL DECONTAMINATION OF VEGETABLE FOODS

[75] Inventors: Eric A. Johnson, Madison, Wis.; Ernani Dell'Acqua; Lorenzo Ferrari, both of Milano, Italy

[73] Assignee: SPA Societa' Prodotti Antibiotici S.p.A., Milan, Italy

[21] Appl. No.: 476,726

[22] Filed: Feb. 8, 1990

[30] Foreign Application Priority Data

Feb. 27, 1989 [IT] Italy .............................. 19564 A/89

[51] Int. Cl.$^5$ ........................................... A23L 3/3463
[52] U.S. Cl. ........................................ 426/52; 426/7
[58] Field of Search ................................ 426/7, 49, 52

[56] References Cited

U.S. PATENT DOCUMENTS 4,810,508  3/1989  Dell'Acqua et al. ................ 426/34

FOREIGN PATENT DOCUMENTS 4729307  8/1972  Japan ..................................... 426/52

OTHER PUBLICATIONS

Hughey et al., "Antibacterial Activity of Hen Egg White Lysozyme Against Listeria Monocytogenes Scott A in Foods", Applied and Environ. Micro., Mar. 1989, pp. 631–638.

*Primary Examiner*—Marianne Cintins
*Attorney, Agent, or Firm*—Oblon, Spivak, McClelland, Maier & Neustadt

[57] ABSTRACT

Process for the decontamination of vegetable foods from *Listeria-sp.* which consists in adding solutions of lysozyme, non-toxic and physiologically compatible salts thereof, to said foods, with or without adjuvant substances, at concentrations suitable for affording decontamination.

5 Claims, 3 Drawing Sheets

PROCESS FOR BACTERIAL DECONTAMINATION OF VEGETABLE FOODS

Object of the present invention is to provide a process of use in the industry of vegetable food-stuffs, usually included in the diet, in order to decontaminate them from highly pathogenic bacteria for human beings.

This technological process consists in the treatment of vegetable foods, particularly those which are commonly called "vegetables", with a solution at varying concentrations of lysozyme enzyme (E.C. 3.2.1.17) or its non-toxic and physiologically compatible salts, with optional addition of adjuvant or synergistic substances, in order to have said foods decontaminated from Listeria-genus bacteria. The Listeria genus has called attention in recent years in consequence of some cases of death by infection caused by the species *Listeria monocytogenes*, which is highly pathogenic indeed for same animals and the man, as recent epidemiological data published in U.S.A. also confimed (Ciesielski C.A. et al. Arch. Internal. Med. 148, 1416, 1988).

Such micro-organism, broadly occurring in the natural world, both in the animal and in the vegetable ones, is gram-positive and belongs to "cocci", although it could also assume the form of a little stick. When observed under a microscope, it is similar to the diphteric bacillus and often it appears in pairs, having a size of $0.5 \times 2$ u. It is a very mobile micro-organism, which hydrolyzes esculin and is catalase-positive. It causes listeriosis which presents tragic aspects in the breast-fed child, when attacking the meninges.

In addition to the monocytogenes genus, it must be remembered *Listeria ivanovii* too, present in the green vegetable foods and very pathogenic for animals, which causes problems in zootechny, particularly the mortal infection of pregnant sheep.

*Listeria monocytogenes* grow very well in a borad range of temperatures, f.e. between 25° C. and 42° C., but it has been reported that Listeria can grow even at lower temperatures (f.e. 4° C.) and over 42° C.

Furthermore, these bacteria can tolerate even high concentrations of NaCl, f.e. 25%.

The Listeria genus can also grow in a broad pH range, f.e. between 5.0 and 9.5.

As far as the epidemiological problem is concerned *Listeria monocytogenes* attacks, particularly some classes at risk, such as babies, pregnant women, immuno-compromised people and wasted away elders. The transmission through food seems to be in natural relation with environmental contamination, particularly through feces or liquids. Although Listeria was once regarded as a classical zoonoses, its ubiquituous diffusion always through food is now established.

The microbiological control of foods and transformation plants has pointed out the possible mutual contamination of the same; thus *Listeria monocytogenes* has been found in the milk at the stable, cheese, eggs, vegetables, ensilated products, sausages, meat, sea-food and poultry. Furthermore, it has been proved that *Listeria monocytogenes* easily contaminates again already industrially treated foods, along the packaging line as in the case of ice-creams, vegetables in bags and salted meats.

As a matter of fact, a 1986 FDA Control regarding 357 plants of food industries pointed out that 2,5% of plants were Listeria contaminated.

The certainty of the decontamination can depend on three factors:

removal of the pathogenic bacterium by means of specific technologies (pasteurization, etc . . . );

protection against re-contamination of the finished food-stuff;

addition of a specific anti-microbial protection based on one or more synergistic agents, which protection can also be repeated for fear of re-contamination to occur.

We have now found that lysozyme of white of egg is active on pathogenic strains of *Listeria monocytogenes*, both in broth and in buffer, for at least four strains, (Scott A. California, V7, $20A_2OHIO$).

It is known that lysozyme is a basic polypeptide, naturally occurring both in the vegetable and animal kingdom, where it performs complex; f.e. immunological and metabolic, activities. In the industry lysozyme is obtained from the white of hen egg, wherein it is contained in amounts ranging between 0.3% and 0.5%.

Its use in the food field is already known, as f.e. in the late swelling of some types of cheese, which phenomenon is due to milk contamination by the spores of particular bacteria, such as *Clostidrium tyrobutirricum*, followed by their growth and germination during the seasoning process of cheese.

This use of lysozyme has been protected (G.B. Patent 2.014.032).

Always in the food field, particularly the dairy farming, the decontamination of milk or other animal products from Listeria was the object of our U.S. patent application No. 07-113,068 of Oct. 27, 1987. As far as the activity of lysozyme on the Listeria genus is concerned, although in vitro activities were previously reported, the possibility of a practical industrial application for decontaminating vegetable foods, which is the object of the present invention, was never envisaged, particularly in the case of *Listeria monocytogenes* and the resulting danger of human, even mortal, infection caused by the same bacterium.

In addition, the present invention also comprises the utilization of other, lysozyme-synergistic substances, such as, for example, the alkali salts of ethylenediaminotetracetic acid, or other chelating, non-toxic substances, such as conalbumin, lactoferrin, transferrins, ceruloplasmin, etc.

As a matter of fact, in the literature Listeria are described as sensitive also to other anti-bacterial substances, such as ampicillin and gentamicin, but the utilization in the food field of these latters, being antibiotics of therapeutic use, cannot be envisaged.

Furthermore, the legislation of many countries forbids the utilization of these and other antibiotics in the field on grounds of toxicity, sensitization or formation of microbial resistances, whereas the utilization of lysozyme in the industry is already allowed in many countries, on account also of its innocuity.

In addition it does not give the vegetable food-stuffs any particular taste or other undesirable organoleptic properties.

Obviously, the possibility of employing lysozyme for the treatment of vetable foods also refers to its salts with non-toxic and pharmaceutically acceptable acids, such as hydrochloride, lactate, phosphate, glycerophosphate, citrate, ascorbate etc. which all suit the purpose of the present invention.

As far as the utilization of lysozyme and its salts jointly with synergistic or adjuvant substances is concerned, some of these substances are already incidentally known in consequence of in vitro microbiologial screenings, but in no case at all their synergistic activity wa observed in tests carried out on vegetable substances, such as lettuce, cabbage, corn, peas, carrots, asparagus, artichokes, etc.

Figure 2:
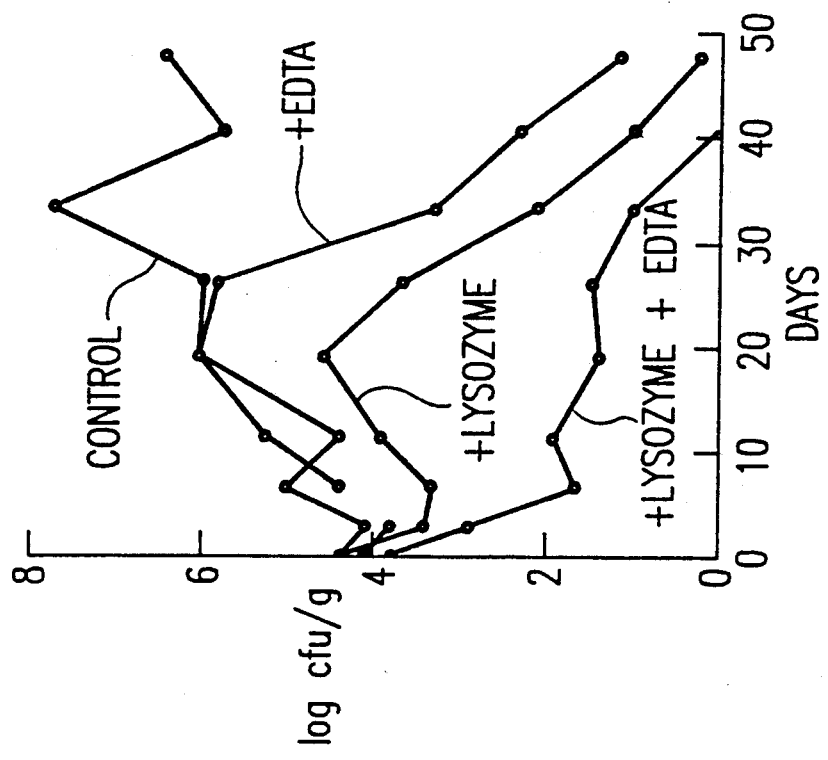
FIG. 2 displays the results obtained in Example 2.
Figure 1:
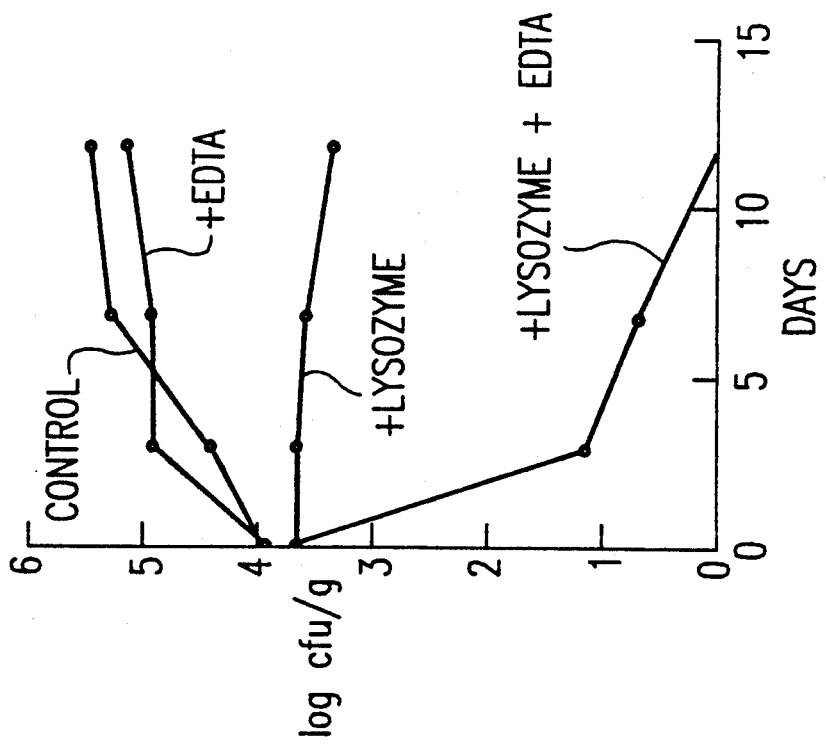
FIG. 1 displays the results obtained in Example 1.
Figure 4:
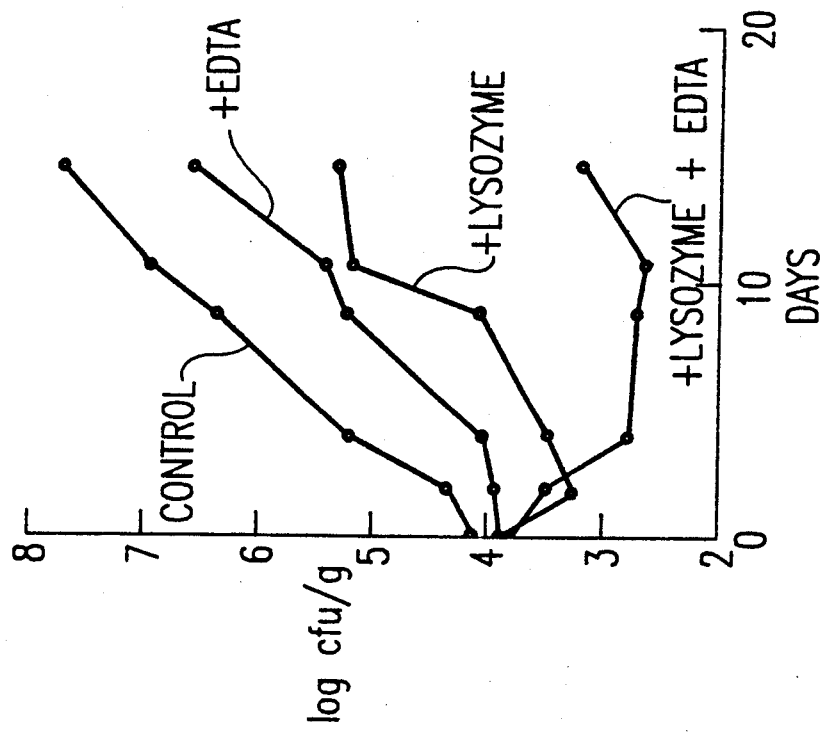
FIG. 4 displays the results obtained in Example 4.
Figure 3:
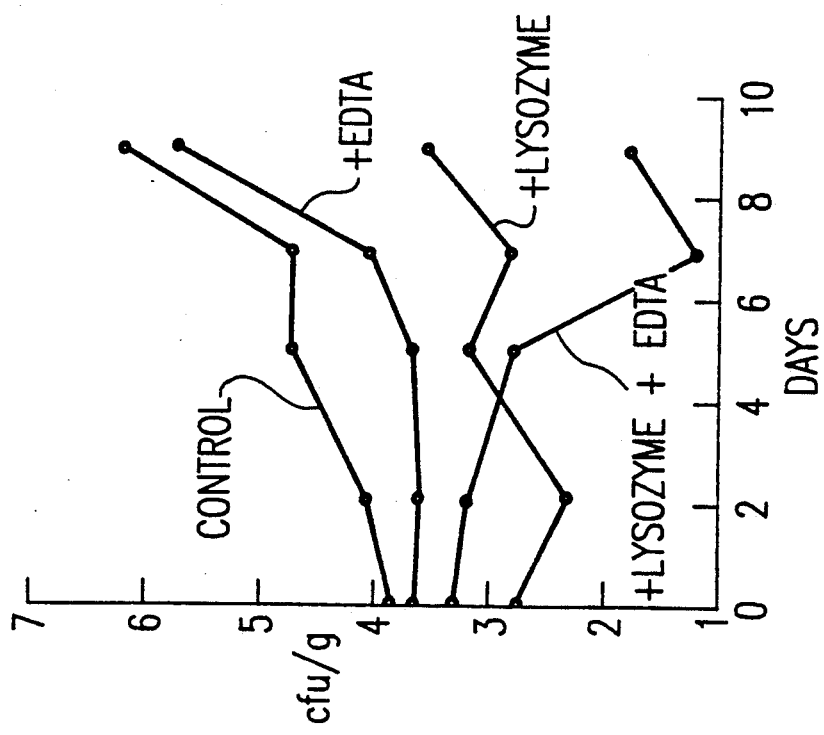
FIG. 3 displays the results obtained in Example 3.

Referring to the methods employed for setting up the process of the present invention and for the appropriate extension and experimental trials, tests were carried out for determining the activity of lysozyme on various strains of *Listeria sp.*, in particular monocytogenes is suitable culture media and on vegetable food-stuffs.

By analytical assays, the stability of lysozyme and its salts in form microbiologically suitable for performing its activity *Listeria sp.* has been proved for the time elapsing from the crop to the consumption of the vegetable food; as target-bacterium, we chose *Listeria monocytogenes* Scott A., from the Collection of Wisconsin Madison University, on account of its utilization also by International Dairy Federation in the methods for identification and counting of *Listeria monocytogenes* in foods.

*Listeria monocytogenes* was cultured in DHI broth static culture of DIFCO Laboratories (Brain-Heart Infusion) at 37° C. The growth in culture medium was measured from the optical density (OD at 500 nm) using a Bausch and Lomb Spectronic 20 spectrophotometer. With the aim of investigating the growth of Listeria monocytogenes (Scott A.) in vegetable food-stuffs, this bacterium was firstly grown in BHI broth at 37° C. and then inoculated in the test-vegetables at a predetermined cell concentration; a concentration of $10^4$ cells per gram of vegetables was employed for an adequate monitoring of its survival capability. All tests on foods were carried out in duplicate. 25 g food samples were analyzed for the presence of Listeria.

The *Listeria monocytogenes* colonies were counted by seeding them directly on agar lithium chloride-phenylethanol-moxalactane medium, which contained glycin.

The counting of colonies (CFU) per gram of vegetables was carried out by placing 25 g samples of vegetables in sterile bags of stomacher plastic with the following addition of 225 ml LEB (Listeria Enrichment Broth) having the following Composition, per liter;

| | |
|---|---|
| Protease Peptone Difco: | 5 g |
| Triptone Difco: | 5 g |
| Yeast extract Difco: | 5 g |
| NaCl: | 20 g |
| Lab. Lemco Powder (OXOID) | 5 g |
| $Na_2H\ PO_4$ | 12 g |
| $KH_2PO_4$ | 1.35 g |
| Esculin (Sigma) | 1 g |
| Seriflavine HCl | 12 mg |
| Nalidixic acid, Sodium salt: | 20 mg |

(Sigma)

The samples were then homogenized for 2 minutes in a Stomacher apparatus (Lab. Blender, mod. 400). 0.1 ml portions were than seeded on 10 lithium chloride - phenylethanol - moxalactame plates. Samples with a too high cell number ($10^4/9$) were repeatedly diluted with 0.01 M phosphate buffer (pH 7.2) and plated as 0.01 ml duplicated samples. The plates were incubated at 20° C. for 5-7 days.

With a too low number of *Listeria monocytogenus* cells an enrichment method was employed.

The Mc Clain and Lee eurichment method was modified by incubating the cultures for 5-7 days at 30° C. in Stomach bags.

A first eurichment was carried out by incubating food homogenates in Stomacher bags at 30° C. for 5-7 days.

Afterwards, 0,1 ml portions of the euriched extract were inoculated in 10 ml of broth for Listeria containing acriflavine hydrochloride (25 mg/1) and incubated for 5-7 days for a further eurichment. These samples were directly smeared on lithium chloride-phenylethanol-moxalactane plates and treated with a solution of potassium hydroxide to select *Listeria monocytogenes*.

In order to prove the identification, five supposed colonies were analyzed for various phenotypic characters including the absence of pigmentation, the morphological appearance on agar tryptose and the catalase-positiveness. Three colonies were then assayed for the characteristic end-over-end motility in tryptose broth at room temperature and for the "umbrella" motility just beneath the surface of Difco medium at room temperature and 37° C. A colony for each sample was then assayed for positiveness in methyl red reaction on MRVP medium (Difco), for esculin hydrolysis in agar bile-esculin (Difco) and for reduction of "litmus-milk" (Difco) after 2 days at 30° C.

Moreover, a serological analysis was carried out, by using Listeria type 4 antiserum. As positive control, Listeria o antigen (Difco type 4) was used.

Strains isolated from vegetables were also assayed on Purple Broth Difco containing 0,5% (w/v) gelactase, sorbitol mannitol, dulcitol, maltose, rhamnose, xylose, glucose, lactose and (+) mellitose and the acid formation mechanism was found to be the same as with Listeria Scott A.

Treatments of vegetables

As substrate for *Listeria monocytogenes* various vegetables were used, some of them being indicated in the following Examples. For all types of food were carried out four tests in duplicate:
controls (without treatment)
lysozyme (100 mg/kg)
EDTA (5 mM)
Lysozyme+EDTA In each test the foods (vegetable) were specially prepared and individually placed in containers to be incubated. Two containers were tested (duplicate samples) at each time of the sampling. All vegetables were incubated with or without experimental inoculation of *Listeria monocytogenes* for determining also the spontaneous contamination of vegetables.

At the completion of the experimental treatments, foods were analyzed for determining the activity of lysozyme. Dried cells of M. Lutens Sigma (0.25 mg/ml) were suspended in 2.9 ml portions of 0.067 M phosphate buffer (pH 6.6).

Samples of vegetables with lysozyme were diluted ten times with phosphate buffer and added to the M. Lutens suspension.

Two hours later the absorbance variations (A 540) was measured. The presence of still active lysozyme was indicated by a marked decrease of absorbance, as compared with not lysozyme-treated samples.

A solution, just prepared, of lysozyme (1-3 ppm) in buffer was used as test. The same solution was then used to established the possible presence of lysozyme activity in not lysozyme-treated vegetables.

The pH of each samples of vegetables was measured after homogenization of 10 g of substance in 90 ml of distilled H$_2$O.

In the following are reported some examples of our studies, which are meant as merely illustrative and by no means limitative of the practical scope of our invention.

The results of each example are reported in form of graphic for sake of brevity and evidence.

EXAMPLE 1

Small bunches of fresh lettuce were carefully cut in stripes and divided in 1800 g portions. Lysozyme was dissolved in 25 ml of 67 mM phosphate buffer, pH 6.6, and EDTA (tetrasodium salt) dissolved in 25 ml of distilled water. The solutions were then sprayed on the 1800 g portions of lettuce.

The final concentrations of lysozyme and EDTA were 100 mg/kg and 5 mM, respectively. *Listeria monocytogenes* was diluted and place in 25 ml of 67 mM phosphate buffer for a final concentration of $1 \times 10^4$ cfu/g lettuce. Lettuce was then accurately blended. 100 g portions of the 50 treated lettuce were placed in 250 ml polystirene containers and incubated at 5° C.

Lettuce samples were analyzed for *Listeria monocytogenes* after 0,3, 7, 12 days (two containers per test were examined at each time of control. The counting of *Listeria monocytogenes* was carried out on two different amounts drawn from each bag. The variability of the two countings was less than twice as much).

The *Listeria monocytogenes* values of the incubated material are reported in FIG. 1.

The lysozyme-EDTA association proved markedly listericide as compared with lysozyme alone, which proved listeriostatic.

Control and samples with EDTA alone showed an increase of *Listeria monocytogenes* up to $3.4 \times 10^5$ and $1.6 \times 10^5$, respectively; on the contrary, samples with EDTA+lysozyme did not present *Listeria monocytogenes* after 12 days.

Samples with lysozyme showed about $2.5 \times 10^3$ *Listeria monocytogenes,* the decrease being 50% of the initial counting.

The experiments on lettuce were carried out for only 12 days, owing to obvious deterioration of vegetables. In samples of lettuce, small variations of pH were observed, with the exception of controls, which showed a lower final pH (4.8) than the treated samples (pH between 5.6 and 5.8).

EXAMPLE 2

Fresh cabbages were prepared as the lettuce of Example 1.

Samples were analyzed on 0, 3, 7, 12, 20, 27, 34, 41, 48 days. The results are reported in FIG. 2.

*Listeria monocytogenes* grows well in chopped cabbages; in the absence of inhibiting substances, the pathogenic micro-organism reaches quickly $3.5 \times 10^6$ cfu/g and then increases up to $10^8$ cfu/g. In incubated samples containing cabbage+100 mg/kg lysozyme or lysozyme+5 mM EDTA, *Listeria monocytogenes* decreases approximately by 10 and 100 times, respectively, after 7 days of incubation at 5° C. As to the samples treated with lysozyme alone, an increase after 7 days was followed by a decrease of the counting of the colonies; on the contrary, samples incubated with lysozyme-+EDTA showed a constant decrease throughout the experiment.

Samples treated with EDTA alone also showed for 30 days a bacterial increase similar to the not treated controls, but afterwards the colonies decreased rapidly.

The unusual increase of *Listeria monocytogenes* in cabbages treated with EDTA alone was often observed also in other foods.

The viability loss of *Listeria monocytogenes* in cabbages, in the presence of lysozyme, with or without EDTA, does not seem to be bound to pH variations, because in all four tests the same trend of pH variations was observed.

The initial pH of cabbages was 4.8, which increased to 6.6-6.8 after 7 days, these values remaining constant up to 20 days from incubation. Afterwards, pH decreased to 4.3-4.9 in samples containing lysozyme as compared to controls which showed, after 40 days, final pH values between 5.8 and 5.85.

Samples treated with EDTA alone showed, after 40 days, pH values ranging between 5.0 and 5.5.

The usual pH variations can be ascribed to alterations caused by *Listeria monocytogenes* or bacterial flora at the refrigeration temperature, the lactic fermentation having been inhibited.

After 1-2 weeks, cabbage appearance changes were observable, such as browning and texture loss. These results suggest that lysozyme+EDTA possesses listericide activity, whereas lysozyme alone is listeriostatic.

EXAMPLE 3

Fresh green beans were chopped in about 2.5-3.8 cm piece.

The following treatment was the same as with lettuce of Example 1. Samples were examined on 0, 2, 5, 7 and 9 days.

Results are graphically reported in FIG. 3.

Lysozyme with EDTA proved bactericide on these vegetables, in fact a 100 times decrease of *Listeria monocytogenes* was observed after one week. In the other tests increases were observed; however, lysozyme slows down this tendency to increase of *Listeria monocytogenes,* as (compared to control and EDTA alone.

Lysozyme with or without EDTA appears on these vegetables less active than on cabbages or lettuce.

Bean initial pH ranged between 5.94 and 6.07. Final pH for all samples was less than 0.4 units different from the initial pH. Therefore, it was the absence of marked pH variations which possible allowed some degree of survival of *Listeria monocytogenes.* Alternatively, one could think that the pieces of the beans were of such size as to binder lysozyme penetration in depth and, therefore, colonies of *Listeria monocytogenes* could have been formed in the center and grown without contacting lysozyme.

EXAMPLE 4

Maize grains, freshly husked, were used. Sampling and lysozyme addition were carried out as in Example 1.

The examinations were carried out on 0, 2, 4, 9, 11, and 15 days.

Results are reported in FIG. 4.

The treatment of fresh maize with lysozyme, with or without EDTA, addition, gave results similar to green beans.

As compared with lettuce and cabbages, the decrease rate of *Listeria monocytogenes* grew up to $1.0 \times 10^7$ and $1.8 \times 10^5$, respectively, after 9 days.

Initial pH of samples ranged between 6.6 and 6.7 and did not change during the first 9 days, but a decrease to 4.5–5.0 was observed in samples not containing EDTA.

In the presence of EDTA, however, pH did not decrease below 6.0, even after 15 days. EDTA seems to have some influence on the deterioration caused by bacteria, but no influence at all on *Listeria monocytogenes* survival. It results from above that lysozyme has a negative influence on the growth of *Listeria monocytogenes* on fresh maize.

The lower rate of decreased of *Listeria monocytogenes* could be due to the different composition of this vegetable food-stuff, such as, for example, the higher content of carbohydrates which possibly aids the growth of *Listeria monocytogenes*.

EXAMPLE 5

Fresh carrots were treated as the lettuce, with the exception that inoculum of *Listeria monocytogenes* was $1 \times 10^3$ cfu/g. Carrots were examined on 0, 2, 5, 9 and 16 days.

Figure 5:
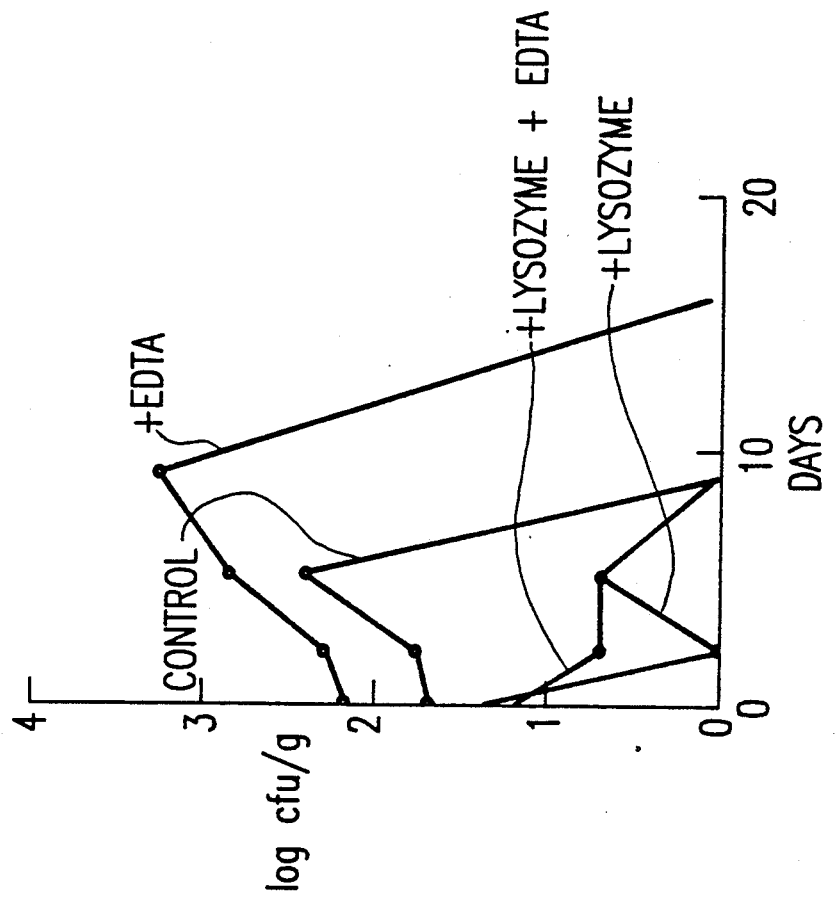
FIG. 5 displays the results obtained in Example 5.

The obtained results are reported in FIG. 5.

In chopped carrots, the incubation with lysozyme, with or without EDTA, and *Listeria monocytogenes* gave anomalous responses, as far as the microbial growth and the bactericide activity are concerned.

In these experiments, *Listeria monocytogenes* was employed at lowed intial levels (about 100 colonies per gram).

Lysozyme alone or lysozyme+EDTA quickly removed *Listeria monocytogenes* from the carrots. The not treated controls showed that initially the bacterial colonies were quickly doubled, with disappearance however after 9 days.

On the contrary, EDTA alone caused an initial increase of the bacterial counting, which then decreased after 9 days.

One could assume the presence in carrots of either chelating agents for metallic ions or listericide substances, synergistic with lysozyme.

The sample initial pH ranged between 6.2 and 6.4. After 9 days a gradual decrease to 4.1–4.4 was diserved. The pH change does not seem to have any influence on *Listeria monocytogenes* survival.

What I claim is:

1. A process for the decontamination of vegetable foods contaminated with Listeria comprising:
    treating the surface of a vegetable with an amount of a solution comprising lysozyme, or salts thereof, and a metal chelating agent, said amount being effective to decontaminate vegetable foods contaminated with Listeria.

2. The process of claim 1, where said vegetable foods are treated on their leaves, seeds or roots.

3. The process of claim 1, wherein *Listeria monocytogenes* is present on the vegetables as a contaminant.

4. The process of claim 1, wherein lysozyme, or salts thereof, are applied in amounts ranging between 20 and 150 mg/kg of vegetable food.

5. The process of claim 1, wherein said metal chelating agent is selected from the group consisting of ethylenediaminotetracetic acid, citric acid and their salts.

* * * * *